United States Patent [19]

Intili

[11] Patent Number: 4,533,435

[45] Date of Patent: Aug. 6, 1985

[54] ANTIMICROBIAL PAPER

[75] Inventor: Henry S. Intili, Lewisville, N.C.

[73] Assignee: Microban Products Company, Winston-Salem, N.C.

[21] Appl. No.: 618,084

[22] Filed: Jun. 7, 1984

[51] Int. Cl.³ .......................... D21D 3/00; D21H 5/22
[52] U.S. Cl. .................... 162/161; 162/168.1; 162/169; 424/19; 424/29; 428/537.5; 428/907
[58] Field of Search ............... 162/161, 169; 428/537.5, 907; 424/19, 29

[56] References Cited

U.S. PATENT DOCUMENTS

| | | | |
|---|---|---|---|
| 2,813,056 | 11/1957 | Davis et al. | 424/132 |
| 2,833,669 | 5/1958 | Ziegler. | |
| 3,959,556 | 5/1976 | Morrison | 428/394 |
| 4,111,922 | 9/1978 | Beede et al. . | |
| 4,343,853 | 8/1982 | Morrison | 428/907 |
| 4,401,712 | 8/1983 | Morrison | 428/907 |

*Primary Examiner*—James C. Cannon
*Attorney, Agent, or Firm*—Charles R. Rhodes; Judith E. Garmon

[57] ABSTRACT

An antimicrobial additive is incorporated into the binding agent of a heavy-duty, kraft-type paper having the characteristics of substantial density, air impermeability, and improved printability. The antimicrobial additive migrates from within the binding agent onto the paper fibers to substantially eliminate growth of microorganisms thereon.

6 Claims, No Drawings

ANTIMICROBIAL PAPER

BACKGROUND OF THE PRESENT INVENTION

The production of antimicrobial paper has generally been accomplished by producing the desired paper in sheet form and then coating the sheet with an antimicrobial coating to inhibit growth of fungi and bacteria thereon. Kraft paper, which is a strong paper made from a sulfate-process woodpulp and frequently used for wrapping paper and shipping cartons, has also been utilized as wrapping paper for surgical instruments and other types of goods which are to be maintained in a sterile condition. When these kraft papers are used for the wrapping of surgical instruments, they are conventionally formed or made in a process that involves brushing the pulp fiber in mixed directions so that the arrangement of fibers creates a tortuous path for any microorganism that attempts to pass through the paper. Upon completion of the paper product the paper is coated with some type of antibacterial or antimicrobial coating to further inhibit the passage of microorganisms from the exterior surfaces of the paper onto the sterile goods packaged therein.

U.S. Pat. No. 2,833,669 is directed to a cellulosic paper material of the type used for medical, industrial, hygenic and other such purposes. This patent discloses the use of a bactericidal coating having a particular affinity for fibrous substances, which coating is spread across the paper product at a point in the procedure just before the fibrous web has been subjected to a drying process. The patent further discloses that the bactericidal layer may be applied to one or both sides of the fibrous web. This patent is somewhat typical of the processes known to exist for producing antimicrobial papers.

The problems inherent in these known processes involve the fact that such coatings are easily rubbed off or otherwise destroyed by unsuitable storage or shipping. Once the coating has been destroyed, there is no further antibacterial action to protect the paper or to inhibit microorganism growth.

It is to overcoming these known deficiencies through the development of an improved antimicrobial paper that the present invention is directed. Modern paper products are generally manufactured from a mixture of various fibers, chiefly of vegetable or cellulosic origin, which fibers are mixed with large quantities of water before being shredded to a very fine consistency. This fibrous mixture is then treated with sizing, a glue-type mixture which makes the finished product water resistant, and fillers such as clay or chalk which are added to give special properties to the paper. In production of the heavier papers such as kraft-type, the basic cellulosic mixture is further subjected to bleaching, pounding and refining, and brushing steps to ensure that the sizing material is deposited almost entirely on the fibrous constitutents and not lost through drainage of water when the material is poured out on screens for the dewatering, pressing, drying, and calendering steps. Further additions to kraft-type papers are binding agents and fillers which improve the color and surface characteristics of the finished paper.

As previously mentioned, the brushing step has been one of the primary methods of improving the ability of the paper to withstand penetration by microorganisms. Another method has been to substantially increase the percentage of binders such as latex, silicone or acrylic materials. The increased percentage of binder closes the spaces between the fibrous material, making it less permeable by microorganisms. However, the brushing step and the increased percentage of binder, both of which are frequently used in the same process, significantly increase the cost of producing the paper.

It has been discovered that the present invention, in addition to improving the antimicrobial characteristics of the paper, also results in a substantial savings in the cost of production by eliminating the need for the brushing operation and/or the increased binder concentration. In the present invention an antimicrobial additive is selected for compatibility with the desired end product and is added to the latex or other binder used in the paper product. The antimicrobial additive is of a type chosen for compatibility with the binder such that it resides in collidal suspension with the amorphous zones of the polymer rather than being cross-linked with the polymer. The result is that reservoirs of antimicrobial additive are established in these amorphous zones and is available to continuously replenish the surface of the paper product as the initial deposits on the surface be utilized or destroyed. Since the additive is in free suspension within the binder, it has the capability of migrating onto adjacent fibers and to the surface of the paper to more uniformly treat and therefore more completely inhibit the growth of bacteria and fungi. The migratory effect of the antimicrobial additive as suspended in the latex or polymer binder has been fully discussed in applicant's prior patents, U.S. Pat. Nos. 3,959,556, 4,343,853, and 4,401,712. The most recent of these patents, U.S. Pat. No. 4,401,712, contains a discussion of the migratory effect as used within a textile material and the entire content of that patent is incorporated by reference herein.

In addition to a kraft-type paper that is inherently antimicrobial throughout, and in addition to the substantial savings in production costs, a further benefit of the present invention is an improved printability of the kraft paper. Historically, kraft papers have been poorly receptive to printing ink because of the high quantities of binder and filler material used therein. The increased concentration of binders and fillers which make the kraft paper substantially water and moisture resistant, and the additional antimicrobial coatings thereon, also make the papers even more resistant to printing processes. Because the antimicrobial additive of the present invention allows for decreasing the percentage of binder used in the paper without decreasing its antibacterial qualities, the resulting paper is substantially more receptive to printing inks.

DETAILED DESCRIPTION OF A PREFERRED EMBODIMENT

The paper formed according to the present invention may be any of a variety of types of paper, made according to a variety of conventional paper forming processes. However, for example, and because a kraft-type paper is traditionally used for packaging surgical instruments and other sterilized materials, this detailed description generally will be directed to the production of a heavy-duty, kraft paper. The kraft process is one generally known as a sulfate pulping process, a wood-pulping process in which sodium sulfate is used in the caustic soda pulp digestion liquor. The resulting paper made by the sulfate pulping processing cannot generally be bleached as white as that made by a soda or sulfite process. However, it produces a strong paper of a dense quality that is substantially air and moisture impermeable.

In the paper making process, raw cellulosic products such as wood, rags, recycled papers, etc., are subjected to the sulfate pulping process, followed by a bleaching procedure most frequently involving the use of hypochlorites and/or chlorine dioxide. After the raw cellulosic products are prepared into a slurry they are further broken down by pounding and refining processes and then mixed with fillers which improve the color and surface characteristics of the finished paper. Preferred filling materials include the aluminum silicates such as kaolin; china clay; titanium dioxides such as rutile and anatase; calcium carbonate; zinc oxide and/or zinc sulfide; calcium sulfate; hydrated aluminum talc; and barium sulfate. The fillers are generally added in quantities of about 1% to 5%–10% parts per weight of fiber material, and are added with more water in about 100–200 parts of water to 1 part of fibrous material. The mixture is constantly stirred with the addition of a sizing compound selected from the group including certain types of soaps, animal glues, starch paste, caseine or synthetic resin glues, latex products, or combinations of two or more of these. As previously mentioned, after the fibers are thus prepared they are laid out and brushed in mixed directions so that their arrangement leads to a tortuous path for microorganisms. The fibers must first be brushed in one direction to improve their mix, and then if the surface of the finished product is to be bonded with adhesive which can be peeled apart to open the package, the fibers must be then brushed in the same direction as the desired peel. However, as previously stated, this brushing step can be eliminated in papers produced according to the present invention. After mixture of the fibrous material with all of the fillers and binders, the pulp material is poured out on a screen (generally an endless wire screen) where it is dewatered, pressed, and calendered to obtain a smooth finish. It is in the steps of adding fillers and binding agents that the present invention is most pertinent.

The interfiber binding agents which are added to the cellulosic pulp material at the time the fillers and sizing additives are presented, are selected from a group including latex polyacrylamides, polyvinyl alcohols and other polymers which are receptive to the selected antimicrobial additive which is to be incorporated into the plastic matrices of the binder. The binding agents named above are conventional and are listed for exemplary purposes only, as the particular binder, apart from compatiblity with the antimicrobial additive, is not the point of novelty.

Once the polymeric binding agent has been selected, the selected antimicrobial additive is added to the base resin and the two are melted together and mixed; or the binding agent is put into solution using a compatible solvent, and then the antimicrobial additive is mixed therein. Upon mixing, the antimicrobial additive becomes incorporated in colloidal suspension within the amorphous zones of the polymeric matrices. Because the two compounds do not cross-link, reservoirs of the antimicrobial additive are formed within these amorphous zones, and become available to replenish the surface of the fibrous product as the supply of additive on the surface of the paper is removed.

Migration from the reservoir is created by destruction or removal of the surface supply of the antimicrobial additive. When the surface system is disturbed, internal vapor pressure on the reservoir causes a small fraction of the additive to migrate toward the surface. Proper migratory action ensures that the growth of bacteria is inhibited across the entire surface of the paper. The presence of moisture on or near the surface of the paper further enhances transfer of the antimicrobial additive because such moisture will soften the cell wall of the bacteria to assist penetration of the additive therethrough, whereupon the additive interferes with the metabolic functioning of the microorganism.

The antimicrobial agent selected for a given binding agent must be able to withstand the temperatures involved in the melting of the binding agent base resin. Further, the additive must be capable of colloidal suspension within the amorphous zones of the polymer as described above. Additives known to be compatible with a variety of contemplated polymers are the halogenated aeromatic nitriles (such as tetrachloroisophthalonitrile); Fungaflor, which is a salt of imazilil sulfate and a proprietary product of Janssen Pharmaceuticals; 3,5,3',4'-tetrachlorosalicylanilide (also known as Irgasan, a product of Ciba-Geigy Company); and dichlorophene (2,2'-methylenebis-4-chlorophenol, a product of the Givaudan Corporation). Of these additives, applicant prefers the use of tetrachloro-isophthalonitrile, and Irgasan. However, other antifungal and antibacterial agents not mentinoed above but which have these same characteristics of colloidal suspension within the polymer may be used.

The antimicrobial additives may be used alone or in combination with each other as active ingredients in the binding agents. The amount used is generally an arbitrary amount, depending on the requirements of a particular application and cost effectiveness. Preferred amounts arrange from 0.1% to 0.5% percentage by weight of the finished paper.

The resulting kraft-type papers have been shown to be effective against gram positive and gram negative bacterial growth and testing has indicated that the effectiveness lasts a substantial period beyond the normal life of the sterilized package made from the paper.

While other modifications of the product described above will be obvious to those skilled in the art, such modifications are believed to fall within the scope of the claims below.

What is claimed is:

1. An antimicrobial paper for packaging surgical supplies and other goods to be maintained in a sterile condition, said paper comprising:
   (a) a slurry of paper forming fibers prepared according to a wetlaid process;
   (b) a polymeric binding agent incorporated in said slurry, said binding agent being selected from the group containing acrylics, polyvinyl acetates, vinyl acetate-ethylenes, polyvinyl chlorides, and styrene-butadine latexes;
   (c) an antimicrobial additive incorporated in said binding agent, said antimicrobial additive being non-crosslinked with said binding agent and forming reservoirs which reside in colloidal suspension within the amorphous zones of said binding agent and from which said antimicrobial additive migrates to the surface of said paper until the reservoir is exhausted;
   (d) fillers selected from the group including aluminum silicates, titanium dioxide, calcium carbonates, zinc oxides, zinc sulfides, hydrated aluminum talc, calcium sulfate, and barium sulfate;

(e) said slurry, binding agents, additives and fillers being subjected to a paper-making process which renders a finished product having the characteristics of substantial density, air impermeability, and smoothness.

2. An antimicrobial paper according to claim 1, wherein said antimicrobial additive is selected from the group consisting of compounds containing halogenated aromatic nitriles; a salt of imazalil sulphate; 3,5,3',4'-tetrachlorosalicylanilide; and dichlorophene.

3. An antimicrobial paper according to claim 2 wherein said antimicrobial additive comprises a combination of two or more of said compounds.

4. An antimicrobial paper for packaging surgical supplies and other goods to be maintained in a sterile condition, said paper comprising the combination of:
   (a) paper forming fibers;
   (b) a polymeric binding agent selected from the group containing acrylics, polyvinyl acetates, vinyl acetate-ethylenes, polyvinyl chlorides, and styrene-butadine latexes;
   (c) said binding agent including an antimicrobial additive incorporated therein, said antimicrobial additive being non-crosslinked with said binding agent and forming reservoirs which reside in colloidal suspension within the amorphous zones of said binding agent and from which said antimicrobial additive migrates to the surface of said paper until the reservoir is exhausted;
   (d) fillers selected from the group including aluminum silicates, titanium dioxide, calcium carbonates, zinc oxides, zinc sulfides, hydrated aluminum talc, calcium sulfate, and barium sulfate;
   (e) said combination having the characteristics of substantial density, air impermeability, and smoothness.

5. An antimicrobial paper according to claim 4, wherein said antimicrobial additive is selected from the group consisting of compounds containing halogenated aromatic nitriles; a salt of imazalil sulphate; 3,5,3',4'-tetrachlorosalicylanilide; and dichlorophene.

6. An antimicrobial paper according to claim 5 wherein said antimicrobial additive comprises a combination of two or more of said compounds.

* * * * *